US012508027B2

(12) United States Patent
Zhang et al.

(10) Patent No.: US 12,508,027 B2
(45) Date of Patent: Dec. 30, 2025

(54) SURGICAL INSTRUMENT

(71) Applicant: INTOCARE MEDICAL TECHNOLOGY (SUZHOU) CO., LTD., Jiangsu (CN)

(72) Inventors: Hui Zhang, Jiangsu (CN); Dianchen Liu, Jiangsu (CN); Yunfeng Du, Jiangsu (CN); Daping Li, Jiangsu (CN)

(73) Assignee: INTOCARE MEDICAL TECHNOLOGY (SUZHOU) CO., LTD., Jiangsu (CN)

( * ) Notice: Subject to any disclaimer, the term of this patent is extended or adjusted under 35 U.S.C. 154(b) by 0 days.

(21) Appl. No.: 18/729,936

(22) PCT Filed: Dec. 15, 2022

(86) PCT No.: PCT/CN2022/139231
§ 371 (c)(1),
(2) Date: Jul. 18, 2024

(87) PCT Pub. No.: WO2023/138269
PCT Pub. Date: Jul. 27, 2023

(65) Prior Publication Data
US 2025/0114093 A1 Apr. 10, 2025

(30) Foreign Application Priority Data
Jan. 24, 2022 (CN) ......................... 202210080845.0

(51) Int. Cl.
*A61B 17/072* (2006.01)
*A61B 17/00* (2006.01)

(52) U.S. Cl.
CPC .................. *A61B 17/07207* (2013.01); *A61B 2017/0084* (2013.01); *A61B 2017/00862* (2013.01);
(Continued)

(58) Field of Classification Search
CPC ................................................ A61B 17/07207
See application file for complete search history.

(56) References Cited

U.S. PATENT DOCUMENTS 4,978,049 A * 12/1990 Green .............. A61B 17/07207 227/21
5,415,334 A * 5/1995 Williamson, IV .......................... A61B 17/07207 227/19
(Continued)

FOREIGN PATENT DOCUMENTS

CN 101224122 A 7/2008
CN 101779977 A 7/2010
(Continued)

*Primary Examiner* — Nathaniel C Chukwurah
(74) *Attorney, Agent, or Firm* — McClure, Qualey & Rodack, LLP

(57) ABSTRACT

A surgical instrument, including an openable/closable staple cartridge and a staple anvil. The staple cartridge has a staple cartridge surface facing the staple anvil (200). The staple cartridge is further provided with a staple recess extending in a direction perpendicular to the staple cartridge surface. A staple and a staple pushing piece are accommodated in the staple recess. The staple pushing piece is arranged at the side of the staple away from the staple cartridge surface, and the staple pushing piece is provided with a staple pushing surface used for contacting the staple so as to push the staple. The staple cartridge is configured such that when the staple pushing piece pushes the staple towards the staple anvil to move to a maximum displacement position, the staple pushing surface of the staple pushing piece is flush with the staple cartridge surface or lower than the staple cartridge surface.

20 Claims, 6 Drawing Sheets

(52) U.S. Cl.
CPC ............... *A61B 2017/00951* (2013.01); *A61B 2017/07264* (2013.01); *A61B 2017/07271* (2013.01)

(56) References Cited

U.S. PATENT DOCUMENTS

| | | | | |
|---|---|---|---|---|
| 7,635,074 | B2 * | 12/2009 | Olson ................ | A61B 17/0682 227/176.1 |
| 7,673,781 | B2 * | 3/2010 | Swayze ................. | B25C 5/0292 227/176.1 |
| 7,845,533 | B2 * | 12/2010 | Marczyk .............. | A61B 17/105 227/181.1 |
| 7,954,685 | B2 * | 6/2011 | Viola ................... | A61B 17/105 227/19 |
| 7,959,051 | B2 * | 6/2011 | Smith .............. | A61B 17/07207 227/176.1 |
| 8,636,766 | B2 * | 1/2014 | Milliman ......... | A61B 17/07207 227/176.1 |
| 10,568,621 | B2 | 2/2020 | Shelton, IV et al. | |
| 2005/0184121 | A1 | 8/2005 | Heinrich | |
| 2011/0084114 | A1 * | 4/2011 | Marczyk ............ | A61B 17/0644 227/178.1 |
| 2011/0180585 | A1 * | 7/2011 | Czernik ........... | A61B 17/07207 227/176.1 |

FOREIGN PATENT DOCUMENTS

| | | | |
|---|---|---|---|
| CN | 103239264 | A | 8/2013 |
| CN | 104027146 | A | 9/2014 |
| CN | 204274541 | U | 4/2015 |
| CN | 107645931 | A | 1/2018 |
| CN | 107645933 | A | 1/2018 |
| CN | 110638498 | A | 1/2020 |
| CN | 111588429 | A | 8/2020 |
| CN | 112353443 | A | 2/2021 |

* cited by examiner

SURGICAL INSTRUMENT

The present application claims the priority of Chinese patent application No. 202210080845.0 filed on Jan. 24, 2022, the disclosure of which is hereby incorporated in its entirety as a part of the present application.

TECHNICAL FIELD

Embodiments of the present disclosure relate to a surgical instrument.

BACKGROUND

With the development of science and technology, more and more surgical instruments have been introduced into surgical and/or medical procedures to replace some traditional manual operations, which greatly improves the efficiency and safety of a surgery. Stapler is one of these surgical instruments. The stapler is a kind of widely applied surgical instrument which can suture a tissue by stapling a plurality of staples arranged in a staggered manner into the tissue as a replacement of manual suturing, and is mainly used in the suture and the stump closure of stomach, duodenum, intestine, colon and the like.

SUMMARY

According to an embodiment of the present disclosure, a surgical instrument is provided, comprising a staple cartridge and a staple anvil that are openable and closable, the staple cartridge includes a cartridge surface facing the staple anvil; the staple cartridge further includes staple recesses extending in a direction perpendicular to the cartridge surface; a staple and a staple pushing piece are accommodated in each staple recess; the staple pushing piece is arranged at a side of the staple away from the cartridge surface, and the staple pushing piece is provided with a staple-pushing surface configured to contact with the staple so as to push the staple; and the staple cartridge is configured such that the staple-pushing surface of the staple pushing piece is flush with or lower than the cartridge surface when the staple pushing piece pushes the staple towards the staple anvil and moves to a maximum displacement position.

For example, the staple-pushing surface is lower than the cartridge surface by 0.25t-2t when the staple pushing piece pushes the staple towards the staple anvil and moves to the maximum displacement position, where t is a dimension of a crossbeam portion of the staple in the direction perpendicular to the cartridge surface.

For example, an end of the staple pushing piece facing the staple includes a groove, the groove includes a bottom and two flanks respectively connected to two opposite sides of the bottom, and a surface of the bottom of the groove is used as the staple-pushing surface; and the two flanks are higher than the cartridge surface when the staple pushing piece pushes the staple towards the staple anvil and moves to the maximum displacement position.

For example, the two flanks are higher than the cartridge surface by 0.05 mm-0.15 mm when the staple pushing piece pushes the staple towards the staple anvil and moves to the maximum displacement position.

For example, the two flanks are a first flank and a second flank, respectively; the first flank and the second flank are configured to clamp the crossbeam portion of the staple; and the first flank and the second flank are further configured such that a clamping force applied on the crossbeam portion of the staple by the first flank and the second flank is smaller than an engagement force between the staple and a target tissue after the staple is sutured to the target tissue.

For example, a surface of the first flank facing the second flank is provided with a first protrusion, a surface of the second flank facing the first flank is provided with a second protrusion, and the first protrusion and the second protrusion are opposite to each other and spaced apart from each other; and the first protrusion and the second protrusion are configured to clamp the crossbeam portion of the staple.

For example, a distance between the first protrusion and the second protrusion is smaller than a dimension of the crossbeam portion of the staple between the first protrusion and the second protrusion by 0.01 mm-0.04 mm.

For example, the crossbeam portion of the staple is clamped by an end of the first flank away from the bottom and an end of the second flank away from the bottom.

For example, a distance between the end of the first flank away from the bottom and the end of the second flank away from the bottom is smaller than a dimension of the crossbeam portion of the staple between the end of the first flank and the end of the second flank by 0.01 mm-0.04 mm.

For example, an elasticity of the first flank and the second flank is greater than an elasticity of other portions of the staple pushing piece except the first flank and the second flank of the staple pushing piece, so that the crossbeam portion of the staple is clamped by the first flank and the second flank of the staple pushing piece as an elastic clamper.

For example, a crossbeam portion of the staple, the bottom of the groove and the two flanks of the groove all extend along a longitudinal direction of the staple cartridge.

For example, at least one of the staple-pushing surface and a crossbeam portion of the staple is provided with an adhesive layer configured to adhere the staple and the staple-pushing surface.

For example, an adhesive force between the staple and the staple-pushing surface is 2-8 times as great as a weight gravity of the staple.

For example, a gap is provided between the staple pushing piece and a recess wall of the staple recess.

For example, the gap between the staple pushing piece and the recess wall of the staple recess is 0.03 mm-0.05 mm.

For example, a lubricating oil layer is provided between the staple pushing piece and a recess wall of the staple recess.

For example, the staple-pushing surface is provided with an adhesive layer configured to adhere the staple and the staple-pushing surface; and the adhesive layer and the lubricating oil layer comprise a same material.

For example, the staple cartridge is configured such that a friction force between the staple pushing piece and a side wall of the staple recess is smaller than or equal to 0.4 N during the staple pushing piece moving towards the staple anvil and moving away from the staple anvil.

For example, the staple anvil includes a guiding groove, and the staple is pushed by the staple pushing piece to collide with the guiding groove so as to be shaped in form; an elastic member is provided at a bottom of the guiding groove, and the elastic member is compressed to generate an elastic deformation during the staple colliding with the guiding groove so as to cause an elastic restoring force.

For example, a tensile strength of the staple pushing piece is greater than or equal to 265 Mpa.

BRIEF DESCRIPTION OF THE DRAWINGS

In order to clearly illustrate the technical solution of the embodiments of the present disclosure, the drawings of the embodiments will be briefly described. It is apparent that the described drawings are only related to some embodiments of the present disclosure and are not limitative of the present disclosure.

DETAILED DESCRIPTION

Figure 1:
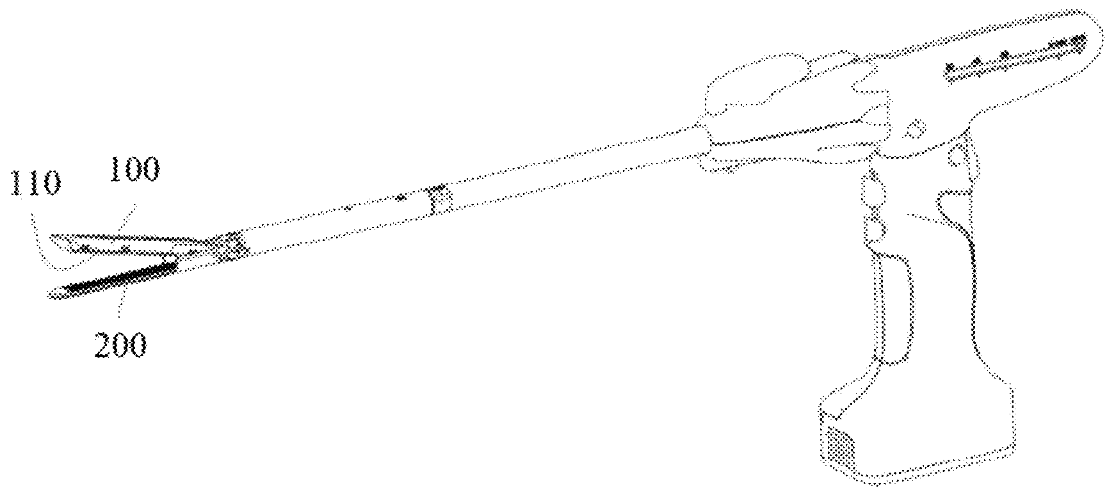
FIG. 1 is a schematic perspective view of a surgical instrument according to an embodiment of the present disclosure.

In order to make the objective, technical solutions, and advantages of the embodiments of the present disclosure clearer, the technical solutions of the embodiments will be described in a clearly and fully understandable way in connection with the related drawings. It is apparent that the described embodiments are just a part but not all of the embodiments of the present disclosure. Based on the described embodiments herein, an ordinary skill in the art can obtain, without any inventive work, other embodiment (s) which is to be within the scope of the present disclosure.

Unless otherwise defined, all the technical and scientific terms used herein have the same meanings as commonly understood by one of ordinary skill in the art to which the present disclosure belongs. The terms, such as "first," "second," or the like, which are used in the present disclosure including the description and claims, are not intended to indicate any sequence, amount or importance, but for distinguishing various components. The terms, such as "comprise/comprising," "include/including," or the like are intended to specify that the elements or the objects stated before these terms encompass the elements or the objects and equivalents thereof listed after these terms, but not preclude other elements or objects. The terms, "on," "under," "left," "right," or the like are only used to indicate relative position relationship, and when the absolute position of the object which is described is changed, the relative position relationship may be changed accordingly.

A surgical instrument (e.g., a stapler) used for suturing a target tissue usually includes a staple cartridge and a staple anvil which are openable and closable, and a plurality of rows of staples are accommodated in the staple cartridge. The process of suturing the target tissue by the surgical instrument mainly includes: closing the staple cartridge and the staple anvil under a drive of a transmission assembly to clamp the target tissue, pushing the staple by a staple pushing piece to fire the staple out of the staple cartridge, and closing and shaping the staple under a compression effect jointly applied by the staple pushing piece and the staple anvil to suture the target tissue, then opening the staple cartridge and the staple anvil under the drive of the transmission assembly to release the sutured target tissue. Generally, in an actual surgical operation, there is a case where a width of the target tissue (the width of the target tissue can be understood as a dimension of the target tissue along a longitudinal direction of the staple cartridge) is smaller than a suturing length of the surgical instrument (the suturing length can be understood as a length of an area of the staple cartridge provided with staples along the longitudinal direction of the staple cartridge). As a result, after all the staples are fired out of the staple cartridge and are closed and shaped, some of these staples are sutured to the target tissue, while some other staples are not sutured to the target tissue and become idle staples. Subsequently, the staple cartridge and the staple anvil are opened, and the idle staples fall and are scattered near the target tissue. A surgeon has to clean these scattered idle staples, which is time-consuming and laborious. If these idle staples cannot be well cleaned, they may remain in the human body all the time after the surgery and cause discomfort of patients and even medical accidents.

Figure 2:
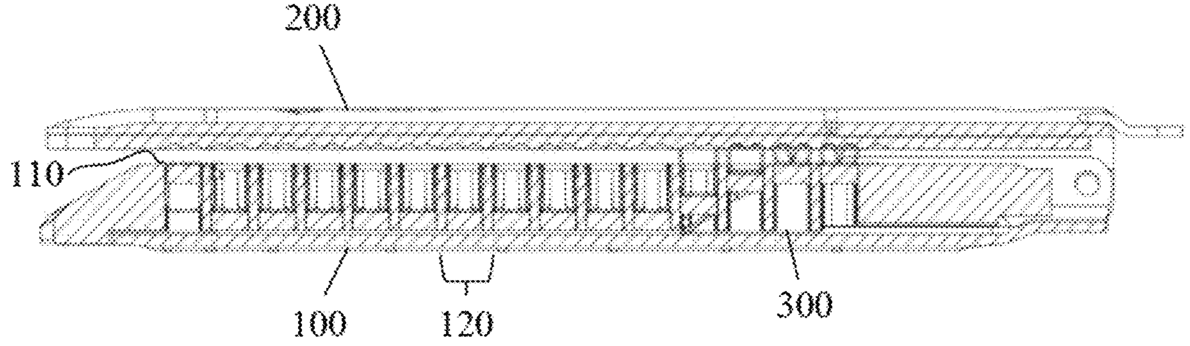
FIG. 2 is a schematic cross-sectional view of a staple cartridge and a staple anvil in a surgical instrument according to an embodiment of the present disclosure.
Figure 3A:
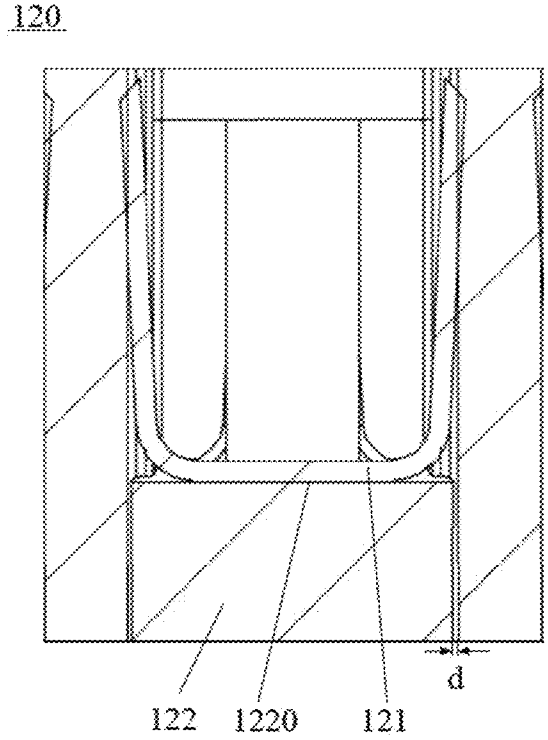
FIG. 3*a* is a schematic cross-sectional view of a staple recess included in a staple cartridge in a surgical instrument according to an embodiment of the present disclosure.
Figure 4A:
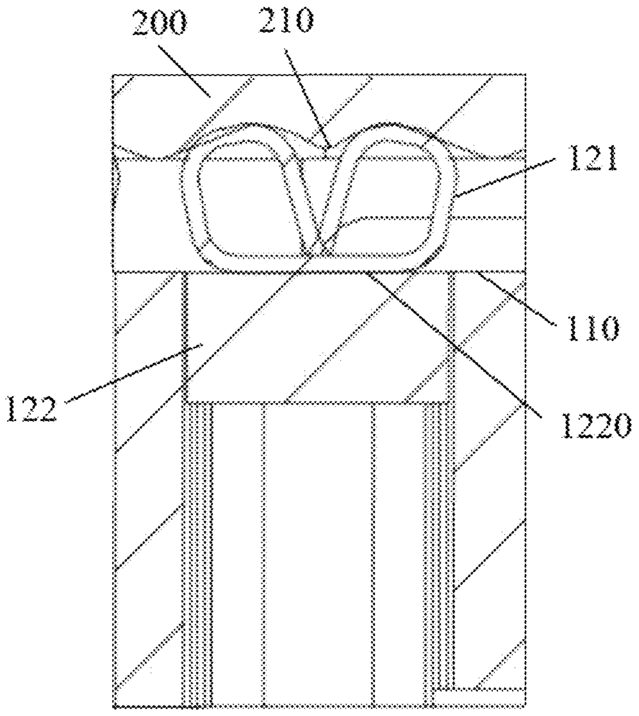
FIG. 4*a* is a schematic cross-sectional view of a surgical instrument according to an embodiment of the present disclosure, in which a staple pushing piece pushes a staple towards a staple anvil and moves to a maximum displacement position.
Figure 4B:
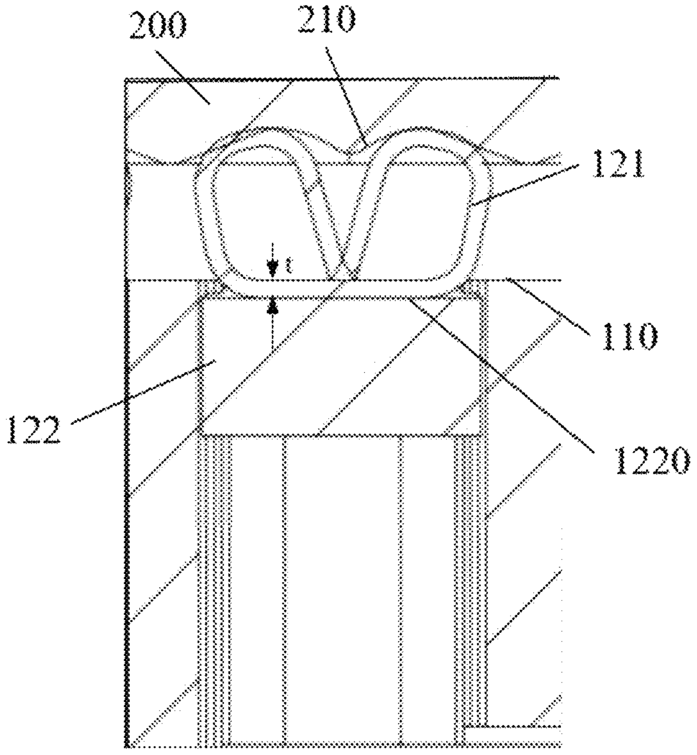
FIG. 4*b* is another schematic cross-sectional view of a surgical instrument according to an embodiment of the present disclosure, in which a staple pushing piece pushes a staple towards a staple anvil and moves to a maximum displacement position.

According to an embodiment of the present disclosure, a surgical instrument is provided. FIG. 1 is a schematic perspective view of a surgical instrument according to an embodiment of the present disclosure; FIG. 2 is a schematic cross-sectional view of a staple cartridge and a staple anvil in a surgical instrument according to an embodiment of the present disclosure; and FIG. 3*a* is a schematic cross-sectional view of a staple recess included in a staple cartridge in a surgical instrument according to an embodiment of the present disclosure. Referring to FIGS. 1 and 2, a surgical instrument according to an embodiment of the present disclosure includes a staple cartridge 100 and a staple anvil 200 which are openable and closable; the staple cartridge 100 includes a cartridge surface 110 facing the staple anvil 200. Referring to FIGS. 2 and 3*a*, the staple cartridge 100 further includes staple recesses 120 extending in a direction perpendicular to the cartridge surface 110, and a staple 121 and a staple pushing piece 122 are accommodated in each staple recess 120. The staple pushing piece 122 is arranged at a side of the staple 121 away from the cartridge surface 110, and the staple pushing piece 122 includes a staple-pushing surface 1220 configured to contact with the staple 121 so as to push the staple 121. The staple cartridge 100 is configured such that when the staple pushing piece 122 pushes the staple 121 towards the staple anvil 200 and moves to a maximum displacement position, the staple-pushing surface 1220 of the staple pushing piece 122 is flush with or lower than the cartridge surface 110. FIGS. 4*a* and 4*b* are schematic cross-sectional views of a surgical instrument according to an embodiment of the present disclosure, respectively, in which the staple pushing piece 122 pushes the staple 121 towards the staple anvil 200 and moves to a maximum displacement position. FIG. 4*a* illustrates the situation that the staple-pushing surface 1220 is flush with the cartridge surface 110 when the staple pushing piece 122 moves to the maximum displacement position, and FIG. 4*b* illustrates the situation that the staple-pushing surface 1220 is lower than the cartridge surface 110 when the staple pushing piece 122 moves to the maximum displacement position.

Figure 5:
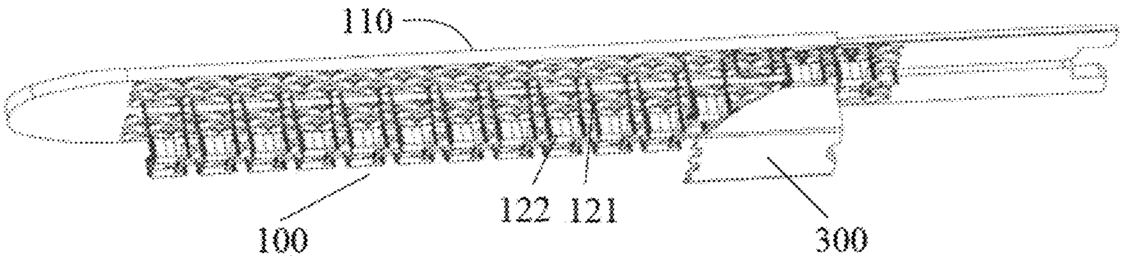
FIG. 5 is a schematic diagram of a staple pushing process of a surgical instrument according to an embodiment of the present disclosure.

According to the surgical instrument of the embodiment of the present disclosure, the idle staples that are not sutured to the target tissue can be held in the staple cartridge without falling scattered, and the specific principle of which will be explained as follows. FIG. 5 is a schematic diagram of a staple pushing process of a surgical instrument according to an embodiment of the present disclosure. Referring to FIGS. 2 and 5, the staple cartridge 100 includes a plurality of staples 121 and a plurality of staple pushing pieces 122 corresponding to the plurality of staples 121. Under the drive of a transmission assembly, the staple cartridge 100 and the staple anvil 200 are closed to clamp the target tissue. Then, under the drive of the transmission assembly, a slider 300 included in the surgical instrument moves from a proximal end to a distal end of the staple cartridge 100 to sequentially drive the plurality of staple pushing pieces 122. The staple pushing pieces 122 driven by the slider 300 push the staples 121 so as to fire the staples 121 out of the staple cartridge 100, and then the staples 121 are closed and shaped in form under a compression effect jointly applied by the staple pushing piece 122 and the staple anvil 200, at which time the staple pushing pieces 122 moving towards the staple anvil 200 arrive at the maximum displacement position. After that, the slider 300 slides over the staple pushing pieces 122, and the staple pushing pieces 122 and the staples 121 lose their support so that the staples 121 will be rebounded towards the staple cartridge 100 and drive the staple pushing pieces 122 to be retreated towards the staple cartridge 100 together. In the surgical instrument according to the embodiment of the present disclosure, because the staple-pushing surface 1220 of the staple pushing piece 122 is flush with or lower than the cartridge surface 110 when the staple pushing piece 122 pushes the staple 121 towards the staple anvil 200 and moves to the maximum displacement position, at least part of the staple 121 that has been closed and shaped in form will enter the inside of the staple recess 120 upon the staple 121 and the staple pushing piece 122 being retreated towards the staple cartridge 100 under the action of the rebound force of the staple 121 due to the slider 300 sliding over the staple pushing piece 122. Subsequently, under the drive of the transmission assembly, the staple cartridge 100 and the staple anvil 200 are opened to release the sutured target tissue. For a staple 121 that has been sutured to the target tissue, the staple will be separated from the staple cartridge 100 and fixed to the target tissue along with the opening of the staple cartridge 100 and the staple anvil 200 under an engagement effect between the staple 121 and the target tissue, even if at least part of the staple 121 has entered the inside of the staple recess 120. For an idle staple that is not sutured to the target tissue, it will still be held in the staple cartridge 100 without falling scattered even if the staple cartridge 100 and the staple anvil 200 are opened, because at least part of the idle staple has entered the staple recess 120 and is held there. In the surgical instrument according to the embodiment of the present disclosure, because the idle staples that are not sutured to the target tissue are held in the staple cartridge 100, which are prevented from being falling scattered, thereby greatly improving the surgical safety; furthermore, it has no need for the surgeon to spend extra time to clean the scattered idle staples, thus greatly improving the surgical efficiency.

Figure 9:
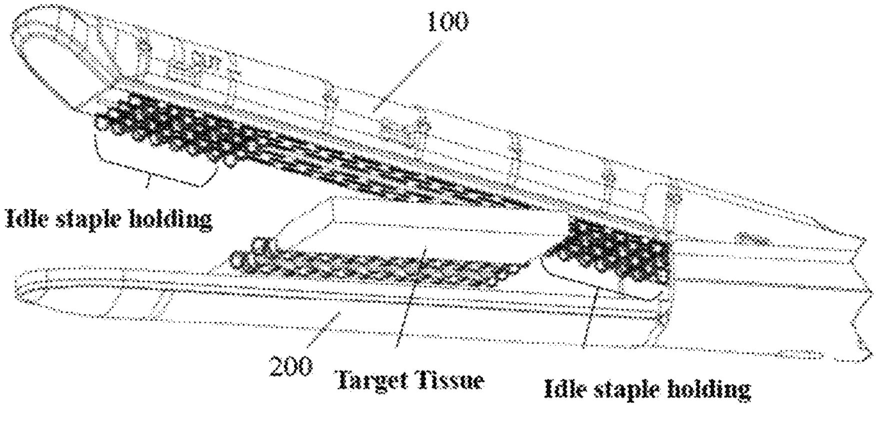
FIG. 9 is a schematic diagram illustrating a suturing effect of a surgical instrument according to an embodiment of the present disclosure.

FIG. 9 is a schematic diagram illustrating a suturing effect of a surgical instrument according to an embodiment of the present disclosure. As can be seen from the figure, the idle staples that are not sutured to a target tissue are stably held in the staple cartridge 100 without falling scattered. The problem that the idle staples fall scattered is commonly existed in the art, and has not been effectively solved yet. Based on the clever use of the phenomenon of "rebound of staple 121", the embodiment of the present disclosure designs such a solution that "the staple-pushing surface 1220 of the staple pushing piece 122 is flush with or lower than the cartridge surface 110 when the staple pushing piece 122 moves to the maximum displacement position", which effectively solves the problem that "the idle staples will fall scattered" in a simple way, and possesses great practical values and application prospects.

For example, FIG. 1 illustrates the case where the staple cartridge 100 and the staple anvil 200 are in an opened state, and FIG. 2 illustrates the case where the staple cartridge 100 and the staple anvil 200 are in a closed state. The opening and closing of the staple cartridge 100 and the staple anvil 200 are driven by the transmission assembly. For example, the transmission assembly is controlled by a control switch arranged on a handle of the surgical instrument.

For example, in the case where the staple-pushing surface 1220 of the staple pushing piece 122 is flush with or lower than the cartridge surface 110, because the staple-pushing surface 1220 of the staple pushing piece 122 is in contact with the staple 121, a surface of a crossbeam portion of the staple 121 that is in contact with the staple-pushing surface 1220 is correspondingly flush with or lower than the cartridge surface 110.

It is to be noted that the target tissue clamped between the staple cartridge 100 and the staple anvil 200 is omitted in FIG. 2 for the convenience of illustration. Due to the existence of the target tissue, there is a gap between the staple cartridge 100 and the staple anvil 200 in FIG. 2. Additionally, FIG. 2 also illustrates the slider 300 moving from the proximal end to the distal end of the staple cartridge 100.

It is to be noted that for the convenience of illustration, the staple anvil 200 and a housing of the staple cartridge 100 are not illustrated in FIG. 5.

It is to be noted that, as illustrated in FIG. 2, the surgical instrument according to the embodiment of the present disclosure includes a plurality of staple recesses 120, and each of the plurality of staple recesses 120 is accommodated with a staple 121 and a staple pushing piece 122. For example, the plurality of staple recesses 120 are arranged in a staggered manner.

It is to be noted that the staple-pushing surface 1220 of the staple pushing piece 122 is not exactly flush with the cartridge surface 110. Considering the existence of the process errors, it is only necessary that the staple-pushing surface 1220 of the staple pushing piece 122 is substantially flush with the cartridge surface 110.

For example, with continued reference to FIG. 4*b*, when the staple pushing piece 122 pushes the staple 121 towards the staple anvil 200 and moves to the maximum displacement position, the staple-pushing surface 1220 is lower than the cartridge surface 110 by 0.25t-2t, where t is a dimension of the crossbeam portion of the staple 121 in a direction perpendicular to the cartridge surface 110. For example, t is 0.15 mm-0.25 mm; further, for example, t is 0.2 mm-0.225 mm. On the one hand, under the condition that the staple-pushing surface 1220 is lower than the cartridge surface 110 when the staple pushing piece 122 moving towards the staple anvil 200 arrives at the maximum displacement position, at least a portion of the staple 121 has been located inside the staple recess 120, and then more portions of the staple 121 will enter the staple recess 120 under the action of a rebound force of the staple 121 as described above, in this way, the idle staple can be held in the staple cartridge 100 more stably; on the other hand, if the staple-pushing surface 1220 is lower than the cartridge surface 110 to a some extent, a height of a portion of the staple 121 located outside the staple recess 120 will be reduced to such an extent as to affect the suturing effect of the staple 121 on the target tissue, which results in that the staple 121 sutured to the target tissue cannot effectively suture the target tissue. Therefore, in order to give consideration to both the stability of holding the idle staple and the suturing effect on the target tissue, in the embodiment of the present disclosure, when the staple pushing piece 122 pushes the staple 121 towards the staple anvil 200 and moves to the maximum displacement position, the staple-pushing surface 1220 is lower than the cartridge surface 110 by 0.25t-2t, so that the staple-pushing surface 1220 is lower than the cartridge surface 110 but not much lower. Further, for example, when the staple pushing piece 122 pushes the staple 121 towards the staple anvil 200 and moves to the maximum displacement position, the staple-pushing surface 1220 is lower than the cartridge surface 110 by 0.05 mm-0.1 mm; in this case, both the stability of holding the idle staples and the suturing effect on the target tissue can be taken into consideration in a better way.

Figure 6:
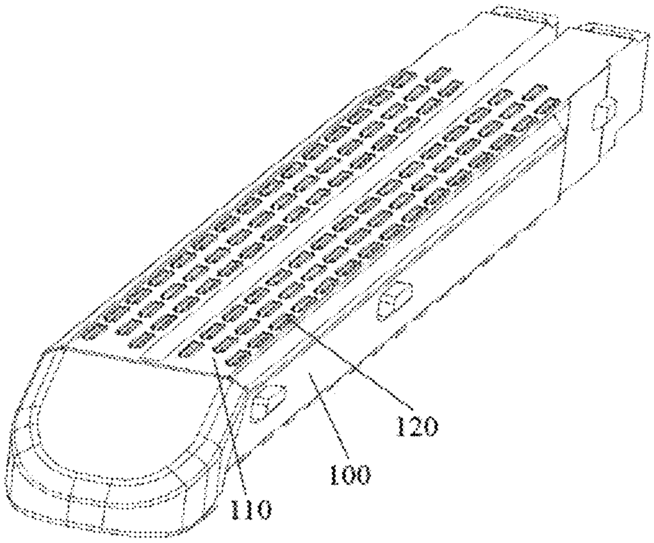
FIG. 6 is a schematic perspective view of a staple cartridge in a surgical instrument according to an embodiment of the present disclosure.
Figure 7A:
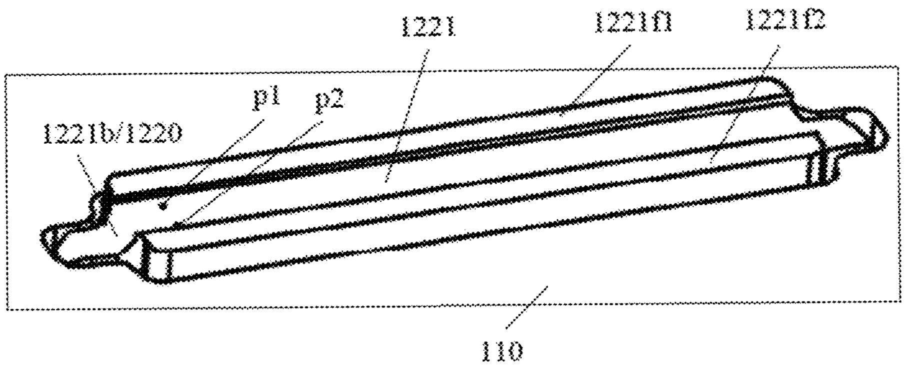
FIG. 7*a* is a schematic perspective view of a groove arranged at an end of a staple pushing piece in a surgical instrument according to an embodiment of the present disclosure.
Figure 7B:
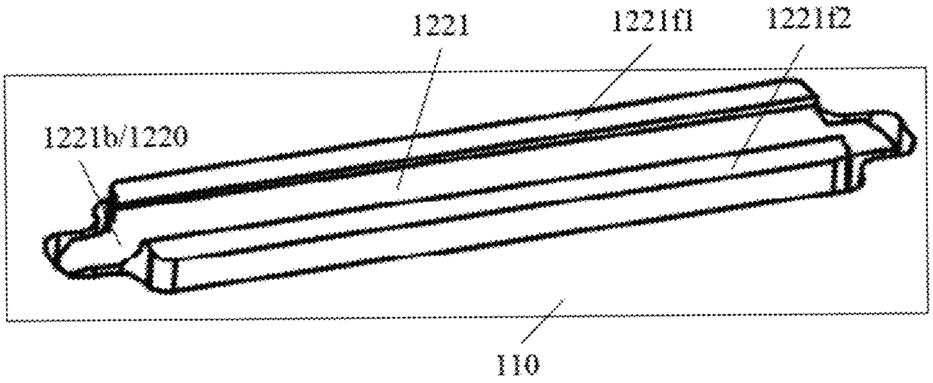
FIG. 7*b* is another schematic perspective view of a groove arranged at an end of a staple pushing piece in a surgical instrument according to an embodiment of the present disclosure.

FIG. 6 is a schematic perspective view of a staple cartridge in a surgical instrument according to an embodiment of the present disclosure; FIG. 7*a* is a schematic perspective view of a groove arranged at an end of a staple pushing piece in a surgical instrument according to an embodiment of the present disclosure; and FIG. 7*b* is another schematic perspective view of the groove arranged at the end of the staple pushing piece in the surgical instrument according to the embodiment of the present disclosure. In FIG. 6, all the staple pushing pieces 122 have been moved towards the staple anvil 200 and arrived at the maximum displacement position, and FIGS. 7*a* and 7*b* respectively illustrate an end of one of the staple pushing pieces 122 in FIG. 6. Referring to FIGS. 6, 7*a* and 7*b*, in the embodiment of the present disclosure, an end of the staple pushing piece 122 facing the staple 121 incudes a groove 1221, the groove 1221 includes a bottom 1221*b* and two flanks 1221*f*1 and 1221*f*2 which are respectively connected to two opposite sides of the bottom 1221*b*, and a surface of the bottom 1221*b* of the groove 1221 is used as the staple-pushing surface 1220 as described above. When the staple pushing piece 122 pushes the staple 121 towards the staple anvil 200 and moves to the maximum displacement position, the two flanks 1221*f*1 and 1221*f*2 are higher than the cartridge surface 110 of the staple cartridge 100. The two flanks 1221*f*1 and 1221*f*2 are higher than the cartridge surface 110 of the staple cartridge 100 when the staple pushing piece 122 pushes the staple 121 towards the staple anvil 200 and moves to the maximum displacement position, in this way, the two flanks 1221*f*1 and 1221*f*2 can guide and restrict the staple 121 and prevent the staple 121 from titling due to compression at the moment of closing and shaping, thus prevent affecting the suturing effect on the target tissue.

Further, for example, when the staple pushing piece 122 pushes the staple 121 towards the staple anvil 200 and moves to the maximum displacement position, the two flanks 1221*f*1 and 1221*f*2 as described above are higher than the cartridge surface 110 of the staple cartridge 100 by 0.05 mm to 0.15 mm. On one hand, as mentioned above, the two flanks 1221*f*1 and 1221*f*2 are higher than the cartridge surface 110 of the staple cartridge 100 when the staple pushing piece 122 moves to the maximum displacement position, so that the two flanks 1221*f*1 and 1221*f*2 can guide and restrict the staple 121; on the other hand, if the two flanks 1221*f*1 and 1221*f*2 are higher than the cartridge surface 110 of the staple cartridge 100 to a some extent when the staple pushing piece 122 moves to the maximum displacement position, the two flanks 1221*f*1 and 1221*f*2 that are higher than the cartridge surface 100 may affect the closing effect between the staple cartridge 100 and the staple anvil 200. For example, the two flanks 1221*f*1 and 1221*f*2 higher than the cartridge surface 100 may cause a gap in at least partial area between the closed staple cartridge 100 and staple anvil 200 to be expanded with weakened closing effect, so that the clamping effect applied on the target tissue by the staple cartridge 100 and the staple anvil 200 is weakened. Therefore, considering both the guiding and restricting effect of the two flanks 1221*f*1 and 1221*f*2 applied on the staple 121 and the closing effect between the staple cartridge 100 and the staple anvil 200, in the embodiment of the present disclosure, when the staple pushing piece 122 pushes the staple 121 towards the staple anvil 200 and moves to the maximum displacement position, the two flanks 1221*f*1 and 1221*f*2 as described above are higher than the cartridge surface 110 of the staple cartridge 100 by 0.05 mm-0.15 mm, so that the two flanks 1221*f*1 and 1221*f*2 are higher than the cartridge surface 110 of the staple cartridge 100 but are not much higher.

For example, the two flanks are a first flank 1221*f*1 and a second flank 1221*f*2, respectively; and the first flank 1221*f*1 and the second flank 1221*f*2 are configured to clamp the crossbeam portion of the staple 121. Because the first flank 1221*f*1 and the second flank 1221*f*2 clamp the crossbeam portion of the staple 121, the idle staple not sutured to the target tissue will be held in the staple cartridge 100 more stably due to the clamping action of the first flank 1221*f*1 and the second flank 1221*f*2, so that the effect of holding the idle staples is enhanced. For example, upon the staple 121 and the staple pushing piece 122 being installed in the staple recess 120, the crossbeam portion of the staple 121 is clamped by the first flank 1221*f*1 and the second flank 1221*f*2. For example, the first flank 1221*f*1 and the second flank 1221*f*2 are also configured such that a clamping force applied on the crossbeam portion of the staple 121 by the first flank 1221*f*1 and the second flank 1221*f*2 is less (for example, much less) than an engagement force between the staple 121 and the target tissue after the staple 121 is sutured to the target tissue, so that even if the first flank 1221*f*1 and the second flank 1221*f*2 clamp the crossbeam portion of the staple 121, it will not obstruct the separation of the staple 121 sutured to the target tissue from the staple cartridge 100 (specifically, from the staple pushing piece 122). Therefore, the embodiment according to the present disclosure gives consideration to both the holding effect on the idle staple and the suturing effect on the target tissue.

For example, in the case where the first flank **1221*f*1 and the second flank 1221*f*2 clamp the crossbeam portion of the staple 121, at least part of the crossbeam portion of the staple 121 will be located in the groove 1221. For example, in the direction perpendicular to the cartridge surface 110, a length of the first flank 1221*f*1 and a length of the second flank 1221*f*2 are respectively smaller than a half of a dimension (i.e., t as described above) of the crossbeam portion of the staple 121, or equal to a half of the dimension of the crossbeam portion of the staple 121, or greater than a half of the dimension of the crossbeam portion of the staple 121; in these cases, the crossbeam portion of the staple 121 has a part located in the groove 1221, and another part located outside the groove. For example, in the direction perpendicular to the cartridge surface 110, the length of the first flank 1221*f*1 and the length of the second flank 1221*f*2 are respectively equal to the dimension of the crossbeam portion, or greater than the dimension of the crossbeam portion; in these cases, the crossbeam portion of the staple 121 is entirely located in the groove 1221**.

For example, in the case where the first flank **1221*f*1 and the second flank 1221*f*2 are configured to clamp the crossbeam portion of the staple 121, the first flank 1221*f*1 and the second flank 1221*f*2 are respectively provided with one or more points in direct abutment with the crossbeam portion of the staple 121**; in the case of multiple direct-abutment points, these multiple direct-abutment points can be separated from each other, or can be continuous with each other to form a direct-abutment surface.

For example, with continued reference to FIG. **7*a*, a surface of the first flank 1221*f*1 facing the second flank 1221*f*2 is provided with a first protrusion p1, and a surface of the second flank 1221*f*2 facing the first flank 1221*f*1 is provided with a second protrusion p2; the first protrusion p1 and the second protrusion p2 are opposite to each other and spaced apart from each other; and the first protrusion p1 and the second protrusion p2 clamp the crossbeam portion of the staple 121. Because the first protrusion p1 and the second protrusion p2 clamp the crossbeam portion of the staple 121, the idle staple not sutured to the target tissue will be held in the staple cartridge 100 more stably due to the clamping action of the first protrusion p1 and the second protrusion p2, so that the effect of holding the idle staples is enhanced. For example, the first protrusion p1 and the second protrusion p2 clamp the crossbeam portion of the staple 121 upon the staple 121 and the staple pushing piece 122 being installed in the staple recess 120. For example, the first protrusion p1 is protruded from the first flank 1221*f*1 towards the second flank 1221*f*2, and the second protrusion p2 is protruded from the second flank 1221*f*2 towards the first flank 1221*f*1**.

For example, with continued reference to FIG. **7*a*, a distance between the first protrusion p1 and the second protrusion p2 is smaller than a dimension of the crossbeam portion of the staple 121 between the first protrusion p1 and the second protrusion p2 by 0.01 mm-0.04 mm. That is, the crossbeam portion of the staple 121 forms an interference fit with a gap between the first protrusion p1 and the second protrusion p2, and the gap between the first protrusion p1 and the second protrusion p2 is smaller than a part of the crossbeam portion of the staple that is to be in interference fit with the gap between the first protrusion p1 and the second protrusion p2 by 0.01 mm-0.04 mm in terms of dimension. On one hand, with the arrangement of the first protrusion p1 and the second protrusion p2, the idle staple can be held in the staple cartridge 100 more stably by utilizing the clamping effect applied on the crossbeam portion of the staple 121 by the first protrusion p1 and the second protrusion p2, so that the effect of holding the idle staples is enhanced; on the other hand, if the first protrusion p1 and the second protrusion p2 apply a strong clamping effect on the crossbeam portion of the staple 121 to a some extent, it will obstruct the separation of the staple 121 sutured to the target tissue from the staple cartridge 100 (specifically, from the staple pushing piece 122), and affect the suturing effect on the target tissue. Therefore, in order to give consideration to both the clamping effect applied on the crossbeam portion of the staple 121 by the first protrusion p1 and the second protrusion p2 and the effect of separating the staple 121 sutured to the target tissue from the staple cartridge 100, in the embodiment according to the present disclosure, the distance between the first protrusion p1 and the second protrusion p2 is designed to be smaller than the dimension of the crossbeam portion of the staple 121 between the first protrusion p1 and the second protrusion p2 by 0.01 mm-0.04 mm, so that the first protrusion p1 and the second protrusion p2 are protruded from the first flank 1221*f*1 and the second flank 1221*f*2, respectively, but are not protruded too much; in this way, the first protrusion p1 and the second protrusion p2 clamp the crossbeam portion of the staple 121 with a clamping force not too large, which ensures that the clamping force applied on the crossbeam portion of the staple 121 by the first flank 1221*f*1 and the second flank 1221*f*2 is smaller (for example, much smaller) than the engagement force between the staple 121** sutured to the target tissue and the target tissue.

For example, in FIG. **7*a*, only one first protrusion p1 and one second protrusion P2 are illustrated as an example. However, the embodiment of the present disclosure is not limited thereto. For example, one pair of first protrusions p1 in which the first protrusions are spaced apart from each other may be provided, and one pair of second protrusions p2 may be provided accordingly, so that the crossbeam portion of the staple 121 is clamped more stably. For example, a plurality of first protrusions p1 spaced apart from each other may be provided, and a plurality of second protrusions p2 spaced apart from each other may be provided accordingly, so that the crossbeam portion of the staple 121 is clamped more stably. However, it is to be noted that no matter how many first protrusions p1 and second protrusions p2 are provided, it is necessary to ensure that the clamping force applied on the crossbeam portion of the staple 121 by the first flank 1221*f*1 and the second flank 1221*f*2 is smaller (for example, much smaller) than the engagement force between the staple 121** sutured to the target tissue and the target tissue.

For example, in FIG. **7*a*, by way of example, both the first protrusion p1 and the second protrusion p2 are illustrated as point-shaped protrusions. However, the embodiment of the present disclosure is not limited thereto. For example, the first protrusion p1 may be a line-shaped protrusion, for example, the line-shaped first protrusion p1 extends along a longitudinal direction of the staple cartridge 100 or extends along a direction intersecting with the longitudinal direction of the staple cartridge 100. Accordingly, for example, the second protrusion p2 may be a line-shaped protrusion, for example, the line-shaped second protrusion p2 extends along the longitudinal direction of the staple cartridge 100 or extends along a direction intersecting with the longitudinal direction of the staple cartridge 100**.

For example, referring to FIG. **7*b*, an end of the first flank 1221*f*1 away from the bottom 1221*b* and an end of the second flank 1221*f*2 away from the bottom 1221*b* clamp the crossbeam portion of the staple 121. Because the ends of the first flank 1221*f*1 and the second flank 1221*f*2 clamp the crossbeam portion of the staple 121, the idle staple not sutured to the target tissue will be held in the staple cartridge 100 more stably due to the clamping action of the first flank 1221*f*1 and the second flank 1221*f*2, so that the effect of holding the idle staples is enhanced. For example, the end of the first flank 1221*f*1 and the end of the second flank 1221*f*2 will clamp the crossbeam portion of the staple 121 upon the staple 121 and the staple pushing piece 122 being installed in the staple recess 120**.

For example, with continued reference to FIG. **7*b*, a distance between an end of the first flank 1221*f*1 away from the bottom 1221*b* and an end of the second flank 1221*f*2 away from the bottom 1221*b* is smaller than a dimension of the crossbeam portion of the staple 121 between the end of the first flank 1221*f*1 and the end of the second flank 1221*f*2 by 0.01 mm-0.04 mm. That is, the crossbeam portion of the staple 121 forms an interference fit with a gap between the end of the first flank 1221*f*1 away from the bottom 1221*b* and the end of the second flank 1221*f*2 away from the bottom 1221*b*, and the gap between the end of the first flank 1221*f*1 away from the bottom 1221*b* and the end of the second flank 1221*f*2 away from the bottom 1221*b* is smaller than a part of the crossbeam portion of the staple to be in interference fit with the gap by 0.01 mm-0.04 mm in terms of dimension. On one hand, the idle staple can be held in the staple cartridge 100 more stably by utilizing the clamping effect applied on the crossbeam portion of the staple 121 by the end of the first flank 1221*f*1 and the end of the second flank 1221*f*2, so that the effect of holding the idle staple can be enhanced; on the other hand, if the end of the first flank 1221*f*1 and the end of the second flank 1221*f*2 apply a strong clamping effect on the crossbeam portion of the staple 121 to a some extent, it will obstruct the separation of the staple 121 sutured to the target tissue from the staple cartridge 100 (specifically, from the staple pushing piece 122) and affect the suturing effect on the target tissue. Therefore, in order to give consideration to both the clamping effect applied on the crossbeam portion of the staple 121 by the end of the first flank 1221*f*1 and the end of the second flank 1221*f*2 as well as the effect of separating the staple 121 sutured to the target tissue from the staple cartridge 100, in the embodiment according to the present disclosure, the distance between the end of the first flank 1221*f*1 and the end of the second flank 1221*f*2 is designed to be smaller than the dimension of the crossbeam portion of the staple 121 between the end of the first flank 1221*f*1 and the end of the second flank 1221*f*2 by 0.01 mm-0.04 mm, so that the end of the first flank 1221*f*1 and the end of the second flank 1221*f*2 can clamp the crossbeam portion of the staple 121, but the clamping force is not too large, thereby ensuring that the clamping force applied on the crossbeam portion of the staple 121 by the first flank 1221*f*1 and the second flank 1221*f*2 is smaller than (for example, much smaller than) the engagement force between the staple 121** sutured to the target tissue and the target tissue.

For example, with continued reference to FIG. **7*b*, the distance between the end of the first flank 1221*f*1 away from the bottom 1221*b* and the end of the second flank 1221*f*2 away from the bottom 1221*b* is smaller than a distance between other portions of the first flank 1221*f*1 and other portions of the second flank 1221*f*2 except the two ends of the first flank 1221*f*1 and the second flank 1221*f*2. In this way, only the end of the first flank 1221*f*1 away from the bottom 1221*b* and the end of the second flank 1221*f*2 away from the bottom 1221*b* clamp the crossbeam portion of the staple 121, while other portions of the first flank 1221*f*1 and the second flank 1221*f*2 do not clamp the crossbeam portion of the staple 121. Therefore, the first flank 1221*f*1 and the second flank 1221*f*2 apply a clamping effect on the crossbeam portion of the staple but the clamping force is not too large, which ensures that the clamping force applied on the crossbeam portion of the staple 121 by the first flank 1221*f*1 and the second flank 1221*f*2 is smaller than (for example, much smaller than) the engagement force between the staple 121** sutured to the target tissue and the target tissue.

For example, an elasticity of the first flank **1221*f*1 and the second flank 1221*f*2 is greater than an elasticity of other portions of the staple pushing piece 122 except the first flank 1221*f*1 and the second flank 1221*f*2, so that the first flank 1221*f*1 and the second flank 1221*f*2 serve as an elastic clamper to clamp the crossbeam portion of the staple 121. That is, the first flank 1221*f*1 and the second flank 1221*f*2 may be respectively provided as clastic members. In this way, on one hand, when the staple 121 and the staple pushing piece 122 are installed in the staple recess 120, an clastic deformation of the first flank 1221*f*1 and the second flank 1221*f*2 can be utilized to conveniently allow the first flank 1221*f*1 and the second flank 1221*f*2 to clamp the crossbeam portion of the staple 121; on the other hand, the elastic deformation of the first flank 1221*f*1 and the second flank 1221*f*2 can also be utilized to conveniently separate the staple 121 sutured to the target tissue from the staple cartridge 100 (specifically, from the staple pushing piece 122). Therefore, both the clamping effect applied on the crossbeam portion of the staple 121 by the first flank 1221*f*1 and the second flank 1221*f*2 as well as the effect of separating the staple 121 sutured to the target tissue from the staple cartridge 100** are taken into consideration.

For example, by setting a thickness of the first flank **1221*f*1 and a thickness of the second flank 1221*f*2 to be smaller than he thickness of other portions of the staple pushing piece 122, the elasticity of the first flank 1221*f*1 and the elasticity of the second flank 1221*f*2 can be made greater than the elasticity of other portions of the staple pushing piece 122**.

For example, a material of the first flank **1221*f*1 and a material of the second flank 1221*f*2 can be selected to be different from those of other portions of the staple pushing piece 122, so that the elasticity of the first flank 1221*f*1 and the elasticity of the second flank 1221*f*2 are greater than that of other portions of the staple pushing piece 122**.

It is to be noted that, as an example in which the first flank **1221*f*1 and the second flank 1221*f*2 clamp the crossbeam portion of the staple 121, the situation where the first protrusion p1 and the second protrusion p2 are provided, the situation where the end of the first flank 1221*f*1 away from the bottom 1221*b* and the end of the second flank 1221*f*2 away from the bottom 1221*b* are utilized, and the situation where the first flank 1221*f*1 and the second flank 1221*f*2 are provided as elastic members are described above with reference to FIG. 6 in combination with FIGS. 7*a* and 7*b*. However, the embodiment of the present disclosure is not intended to limit the manner in which the first flank 1221*fl* and the second flank 1221*f*2 clamp the crossbeam portion of the staple 121, as long as the first flank 1221*fl* and the second flank 1221*f*2 clamp the crossbeam portion of the staple 121 with a clamping force smaller than (for example, much smaller than) the engagement force between the staple 121 and the target tissue after the staple 121** is sutured to the target tissue.

For example, with continued reference to FIGS. 6, 7*a* and 7*b*, the crossbeam portion of the staple 121, the bottom 1221*b* of the groove 1221, and the two flanks 1221*f*1 and 1221*f*2 of the groove 1221 all extend along the longitudinal direction of the staple cartridge 100. In this way, the two flanks 1221*f*1 and 1221*f*2 can function to guide and restrict the staple 121 in a better way, so as to prevent the staple 121 from tilting due to the compression at the moment of closing and shaping, and hence to prevent from affecting the suturing effect on the target tissue. For example, the longitudinal direction of the staple cartridge 100 is a direction from a proximal end to a distal end of the staple cartridge 100; the proximal end of the staple cartridge 100 is an end of the staple cartridge 100 close to an operator (e.g., the surgeon) of the surgical instrument, while the distal end of the staple cartridge 100 is an end of the staple cartridge 100 away from the operator (e.g., the surgeon) of the surgical instrument.

For example, in FIGS. 7*a* and 7*b*, it is illustrated that the first flank 1221*f*1 is a continuous strip extending along the longitudinal direction of the staple cartridge 100, and the second flank 1221*f*2 is a continuous strip extending along the longitudinal direction of the staple cartridge 100. However, the embodiment of that present disclosure is not limited thereto. The first flank 1221*f*1 and the second flank 1221*f*2 may be arranged discontinuously along the longitudinal direction of the staple cartridge 100. For example, along the longitudinal direction of the staple cartridge 100, the first flank 1221*f*1 includes a plurality of first teeth spaced apart from each other, and the second flank 1221*f*2 includes a plurality of second teeth spaced apart from each other, and each of the first teeth and each of the second teeth are extending from the bottom 1221*b* of the groove 1221 towards the staple 121. For example, in a direction perpendicular to the longitudinal direction of the staple cartridge 100, the plurality of first teeth are arranged in directly opposite to the plurality of second teeth, respectively. For example, in the longitudinal direction of the staple cartridge 100, the plurality of first teeth and the plurality of second teeth are staggered with each other. For example, the plurality of first teeth have the same dimension and the same shape, or have different dimensions and different shapes from each other. For example, the plurality of second teeth have the same dimension and the same shape, or have different dimensions and different shapes from each other. For example, one first tooth and one second tooth have the same dimension and the same shape, or have different dimensions and different shapes from each other.

For example, in FIGS. 7*a* and 7*b*, the first flank 1221*f*1 and the second flank 1221*f*2 have relatively regular shapes. However, the embodiment of the present disclosure is not limited to this, and the first flank 1221*f*1 and the second flank 1221*f*2 may have any shapes.

For example, in FIGS. 7*a* and 7*b*, it is illustrated that the first flank 1221*f*1 and the second flank 1221*f*2 are located at two opposite sides of the bottom 1221*b* in the direction perpendicular to the longitudinal direction of the staple cartridge 100. However, the embodiment of the present disclosure is not limited thereto, and the first flank 1221*f*1 and the second flank 1221*f*2 may be located at two opposite sides of the bottom 1221*b* in the longitudinal direction of the staple cartridge 100.

Figure 3B:
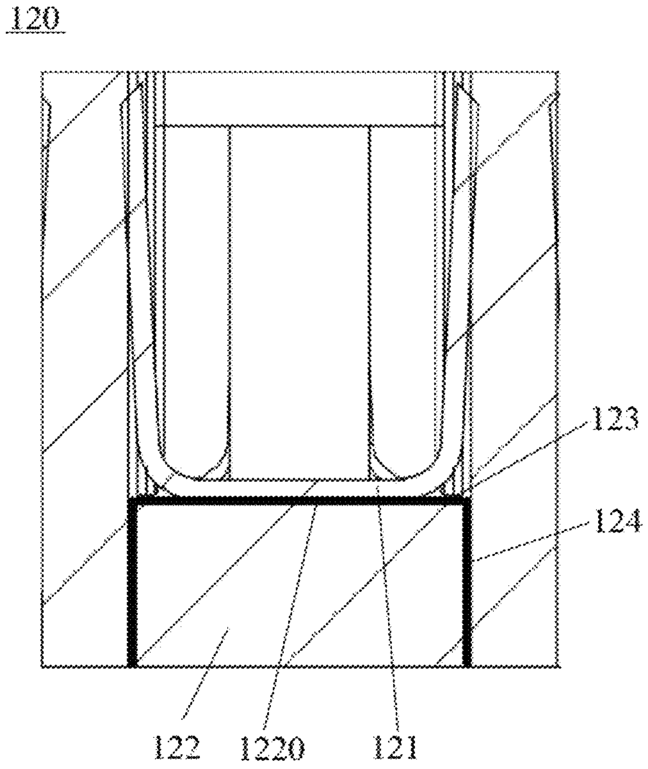
FIG. 3*b* is another schematic cross-sectional view of a staple recess included in a staple cartridge in a surgical instrument according to an embodiment of the present disclosure.

For example, in FIGS. 7*a* and 7*b*, it is illustrated that the first flank 1221*f*1 is arranged in directly opposite to the second flank 1221*f*2 in the direction perpendicular to the longitudinal direction of the staple cartridge 100. However, the embodiment of the present disclosure is not limited to this, and at least part of the first flank 1221*f*1 may not be directly opposite to the second flank 1221*f*2 in the direction perpendicular to the longitudinal direction of the staple cartridge 100. FIG. 3*b* is another schematic cross-sectional view of the staple recess included in the staple cartridge in the surgical instrument according to the embodiment of the present disclosure. For example, referring to FIG. 3*b*, at least one of the staple-pushing surface 1220 and the crossbeam portion of the staple 121 is provided with an adhesive layer 123 for adhering the staple 121 and the staple-pushing surface 1220. With the arrangement of the adhesive layer 123, the idle staple not sutured to the target tissue will be held in the staple cartridge 100 more stably due to an adhesive effect of the adhesive layer 123, so that the effect of holding the idle staples is enhanced. For example, the adhesive layer 123 will adhere the crossbeam portion of the staple 121 onto the staple-pushing surface 1220 upon the staple 121 and the staple pushing piece 122 being installed in the staple recess 120.

Further, for example, an adhesive force between the staple 121 and the staple-pushing surface 1220 is 2-8 times as great as the weight gravity of the staple 121. On one hand, with the arrangement of the adhesive layer 123, the idle staple can be held in the staple cartridge 100 more stably by utilizing the adhesive effect applied on the staple 121 by the adhesive layer 123, so that the effect of holding the idle staples is enhanced; on the other hand, if the adhesive layer 123 applies a strong adhesive effect on the staple 121 to a some extent, it will obstruct the separation of the staple 121 sutured to the target tissue from the staple cartridge 100 (specifically, from the staple pushing piece 122) and hence affect the suturing effect on the target tissue. Therefore, in order to give consideration to both the adhesively holding effect applied on the staple 121 by the adhesive layer 123 and the effect of separating the staple 121 sutured to the target tissue from the staple cartridge 100, in the embodiment according to the present disclosure, the adhesive force between the staple 121 and the staple-pushing surface 1220 is set to be 2-8 times as great as the weight gravity of the staple 121, so that the adhesive layer 123 can adhere the staple 121, but the adhesive force is not too large.

For example, with continued reference to FIG. 3*a*, there is a gap d between the staple pushing piece 122 and a recess wall of the staple recess 120. As mentioned above, when the slider 300 slides over the staple pushing piece 122, the staple pushing piece 122 and the staple 121 lose their support, and the staple 121 will be rebounded towards the staple cartridge 100 and drive the staple pushing piece 122 to be retreated towards the staple cartridge 100 together, so that at least part of the closed and shaped staple 121 will enter the staple recess 120, and finally the idle staples not sutured to the target tissue will be held in the staple cartridge 100 without falling scattered. By providing the gap d between the staple pushing piece 122 and the recess wall of the staple recess 120, a friction force between the staple pushing piece 122 and the recess wall of the staple recess 120 can be reduced or even avoided to reduce a resistance against the staple 121 which is rebounded to be retreated into the staple cartridge 100, so that the staple 121 can be retreated into the staple recess 120 more smoothly, thereby ensuring that the idle staples can be held in the staple cartridge 100.

Further, for example, the gap d between the staple pushing piece 122 and the recess wall of the staple recess 120 is 0.03 mm-0.05 mm. On one hand, as mentioned above, by setting the gap d between the staple pushing piece 122 and the recess wall of the staple recess 120, it can reduce the resistance against the staple 121 which is rebounded to be retreated towards the staple cartridge 100, so that the staple

121 can be retreated into the staple recess 120 more easily; on the other hand, if the gap between the staple pushing piece 122 and the recess wall of the staple recess 120 is large to some extent, the area of the staple-pushing surface 1220 will be significantly reduced, which will affect the effect of pushing the staple and affect the stability of installing the staple pushing piece 122 in the staple recess 120. Therefore, in the embodiment according to the present disclosure, in order to give consideration to both of reducing the resistance against the staple 121 retreating towards the staple cartridge 100, as well as ensuring the effect of pushing the staple and the stability of installing the staple pushing piece 122, the gap d between the staple pushing piece 122 and the recess wall of the staple recess 120 is set to be 0.03 mm-0.05 mm; that is, a gap is provided between the staple pushing piece 122 and the recess wall of the staple recess 120, but the gap is not too large.

For example, with continued reference to FIG. 3*b*, a lubricating oil layer 124 is provided between the staple pushing piece 122 and the recess wall of the staple recess 120. As mentioned above, when the slider 300 slides over the staple pushing piece 122, the staple pushing piece 122 and the staple 121 lose their support, and the staple 121 will be rebounded towards the staple cartridge 100 and drive the staple pushing piece 122 to be retreated towards the staple cartridge 100 together, so that at least part of the closed and shaped staple 121 will enter the staple recess 120, and finally the idle staples not sutured to the target tissue will be held in the staple cartridge 100 without falling scattered. By arranging the lubricating oil layer 124 between the staple pushing piece 122 and the recess wall of the staple recess 120, it can reduce the friction force between the staple pushing piece 122 and the recess wall of the staple recess 120, and hence reduce the resistance against the staple 121 which is rebounded to be retreated towards the staple cartridge 100, so that the staple 121 can be retreated into the staple recess 120 more smoothly, thereby ensuring that the idle staples can be held in the staple cartridge 100.

For example, the lubricating oil layer 124 includes the same material as the adhesive layer 123 described above. In this way, the manufacturing process of the adhesive layer 123 and the lubricating oil layer 124 can be simplified, so that the technical solution according to the embodiment of the present disclosure is more convenient to implement. For example, both the adhesive layer 123 and the lubricating oil layer 124 are medical greases.

For example, according to the embodiment of the present disclosure, the staple cartridge 100 is configured such that a friction force between the staple pushing piece 122 and a side wall of the staple recess 120 is smaller than or equal to 0.4 N during the staple pushing piece 122 moving towards the staple anvil 200 and moving away from the staple anvil 200. The inventors of the present application found that, by setting the friction force between the staple pushing piece 122 and the side wall of the staple recess 120 as small as possible, for example, by setting the friction force to be smaller than or equal to 0.4 N, it can also reduce the resistance against the staple 121 which is rebounded to be retreated towards the staple cartridge 100, so that the staple 121 can be retreated into the staple recess 120 more smoothly and the idle staples can be held in the staple cartridge 100. Additionally, by setting the friction force between the staple pushing piece 122 and the side wall of the staple recess 120 to be smaller than or equal to 0.4 N, it can also reduce the resistance when the staple pushing piece 122 pushes the staple towards the staple anvil 200, ensure that the staple 121 can be fired out of the staple cartridge 100 smoothly and the suturing effect of the staple 121 applied on the target tissue.

Figure 8:
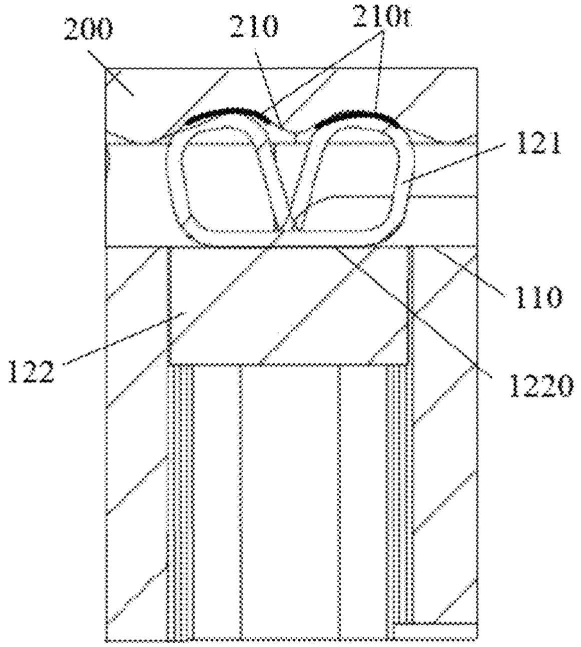
FIG. 8 is yet another schematic cross-sectional view of a surgical instrument according to an embodiment of the present disclosure, in which a staple pushing piece pushes a staple towards a staple anvil and moves to a maximum displacement position.

FIG. 8 is yet another schematic cross-sectional view of the surgical instrument according to the embodiment of the present disclosure in which the staple pushing piece pushes the staple towards the staple anvil and moves to the maximum displacement position. For example, referring to FIG. 8, the staple anvil 200 includes a guiding groove 210 for shaping the staple, and the staple 121 is pushed by the staple pushing piece 122 to collide with the guiding groove 210 so as to be shaped in form. An elastic member 210*t* is provided at a bottom of the guiding groove 210, and is compressed to generate an elastic deformation which causes an elastic restoring force during the process of the staple 121 colliding with the guiding groove 210. With the arrangement of the elastic member 210*t*, when the slider 300 slides over the staple pushing piece 122, the staple pushing piece 122 and the staple 121 will lose their support, and the elastic member 210*t* will push the staple 121 and the staple pushing piece 122 to move towards the staple cartridge 100 under the action of the elastic restoring force thereof. In this case, it can be understood that the staple 121 is subjected to an enhanced rebound force, so that the closed and shaped staple 121 can be retreated into the staple recess 120 more deeply, and the effect of holding the idle staples is enhanced. For example, the clastic member 120*t* may be an elastic resin pad, an elastic metal piece, etc.

For example, according to the embodiment of the present disclosure, a tensile strength of the staple pushing piece 122 is greater than or equal to 265 Mpa. As described above, according to the embodiment of the present disclosure, in order to hold the idle staples in the staple cartridge 100 without falling scattered, the staple-pushing surface 1220 of the staple pushing piece 122 is flush with or lower than the cartridge surface 110 when the staple pushing piece 122 pushes the staple 121 towards the staple anvil 200 and moves to the maximum displacement position, which is totally different from the situation in the conventional way of pushing the staple that "the staple-pushing surface of the staple pushing piece is higher than the cartridge surface when the staple pushing piece moves to the maximum displacement position". Therefore, in order to ensure that the compression force applied on the staple 121 when the staple 121 is compressed and shaped in form in the embodiment of the present disclosure is substantially the same as the compression force applied on the staple in the conventional way of pushing the staple in which "the staple-pushing surface is higher than the cartridge surface", the embodiment of the present disclosure increases the strength of the staple pushing piece 122, i.e., the tensile strength of the staple pushing piece 122 is set to be greater than or equal to 265 Mpa, so that the shaping effect applied on the staple 121 sutured to the target tissue can be ensured while realizing the effect of holding the idle staples.

Without conflicting with each other, various solutions and features according to the embodiments of the present disclosure as described above can be combined with each other.

What have been described above are only exemplary embodiments of the present disclosure, which are not intended to limit the scope of the present disclosure, and the scope of the present disclosure is determined by the claims.

What is claimed is:

1. A surgical instrument, comprising a staple cartridge and a staple anvil that are openable and closable, wherein the staple cartridge includes a cartridge surface facing the staple anvil;

the staple cartridge further includes staple recesses extending in a direction perpendicular to the cartridge surface; a staple and a staple pushing piece are accommodated in each staple recess; the staple pushing piece is arranged at a side of the staple away from the cartridge surface, and the staple pushing piece is provided with a staple-pushing surface configured to contact with the staple so as to push the staple; and the staple cartridge is configured such that the staple-pushing surface of the staple pushing piece is lower than the cartridge surface when the staple pushing piece pushes the staple towards the staple anvil and arrives at a maximum displacement position.

2. The surgical instrument according to claim 1, wherein the staple-pushing surface is lower than the cartridge surface by 0.25t-2t when the staple pushing piece pushes the staple towards the staple anvil and moves to the maximum displacement position, where t is a dimension of a crossbeam portion of the staple in the direction perpendicular to the cartridge surface.

3. The surgical instrument according to claim 1, wherein an end of the staple pushing piece facing the staple includes a groove, the groove includes a bottom and two flanks respectively connected to two opposite sides of the bottom, and a surface of the bottom of the groove is used as the staple-pushing surface; and the two flanks are higher than the cartridge surface when the staple pushing piece pushes the staple towards the staple anvil and moves to the maximum displacement position.

4. The surgical instrument according to claim 3, wherein the two flanks are higher than the cartridge surface by 0.05 mm-0.15 mm when the staple pushing piece pushes the staple towards the staple anvil and moves to the maximum displacement position.

5. The surgical instrument according to claim 3, wherein the two flanks are a first flank and a second flank, respectively;

the first flank and the second flank are configured to clamp the crossbeam portion of the staple; and the first flank and the second flank are further configured such that a clamping force applied on the crossbeam portion of the staple by the first flank and the second flank is smaller than an engagement force between the staple and a target tissue after the staple is sutured to the target tissue.

6. The surgical instrument according to claim 5, wherein a surface of the first flank facing the second flank is provided with a first protrusion, a surface of the second flank facing the first flank is provided with a second protrusion, and the first protrusion and the second protrusion are opposite to each other and spaced apart from each other; and the first protrusion and the second protrusion are configured to clamp the crossbeam portion of the staple.

7. The surgical instrument according to claim 6, wherein a distance between the first protrusion and the second protrusion is smaller than a dimension of the crossbeam portion of the staple between the first protrusion and the second protrusion by 0.01 mm-0.04 mm.

8. The surgical instrument according to claim 5, wherein the crossbeam portion of the staple is clamped by an end of the first flank away from the bottom and an end of the second flank away from the bottom.

9. The surgical instrument according to claim 8, wherein a distance between the end of the first flank away from the bottom and the end of the second flank away from the bottom is smaller than a dimension of the crossbeam portion of the staple between the end of the first flank and the end of the second flank by 0.01 mm-0.04 mm.

10. The surgical instrument according to claim 5, wherein an elasticity of the first flank and the second flank is greater than an elasticity of other portions of the staple pushing piece except the first flank and the second flank of the staple pushing piece, so that the crossbeam portion of the staple is clamped by the first flank and the second flank of the staple pushing piece as an elastic clamper.

11. The surgical instrument according to claim 3, wherein a crossbeam portion of the staple, the bottom of the groove and the two flanks of the groove all extend along a longitudinal direction of the staple cartridge.

12. The surgical instrument according to claim 1, wherein at least one of the staple-pushing surface and a crossbeam portion of the staple is provided with an adhesive layer configured to adhere the staple and the staple-pushing surface.

13. The surgical instrument according to claim 12, wherein an adhesive force between the staple and the staple-pushing surface is 2-8 times as great as a weight gravity of the staple.

14. The surgical instrument according to claim 1, wherein a gap is provided between the staple pushing piece and a recess wall of the staple recess.

15. The surgical instrument according to claim 14, wherein the gap between the staple pushing piece and the recess wall of the staple recess is 0.03 mm-0.05 mm.

16. The surgical instrument according to claim 1, wherein a lubricating oil layer is provided between the staple pushing piece and a recess wall of the staple recess.

17. The surgical instrument according to claim 16, wherein the staple-pushing surface is provided with an adhesive layer configured to adhere the staple and the staple-pushing surface; and the adhesive layer and the lubricating oil layer comprise a same material.

18. The surgical instrument according to claim 1, wherein the staple cartridge is configured such that a friction force between the staple pushing piece and a side wall of the staple recess is smaller than or equal to 0.4 N during the staple pushing piece moving towards the staple anvil and moving away from the staple anvil.

19. The surgical instrument according to claim 1, wherein the staple anvil includes a guiding groove, and the staple is pushed by the staple pushing piece to collide with the guiding groove so as to be shaped in form;

an elastic member is provided at a bottom of the guiding groove, and the elastic member is compressed to generate an elastic deformation during the staple colliding with the guiding groove so as to cause an elastic restoring force; and wherein a tensile strength of the staple pushing piece is greater than or equal to 265 Mpa.

20. A surgical instrument, comprising a staple cartridge and a staple anvil that are openable and closable, wherein the staple cartridge includes a cartridge surface facing the staple anvil;

the staple cartridge further includes staple recesses extending in a direction perpendicular to the cartridge surface; a staple and a staple pushing piece are accommodated in each staple recess; the staple pushing piece is arranged at a side of the staple away from the cartridge surface, and the staple pushing piece is provided with a staple-pushing surface configured to contact with the staple so as to push the staple; and the staple cartridge is configured such that the staple-pushing surface of the staple pushing piece is lower than the cartridge surface by 0.25t-2t when the staple pushing piece pushes the staple towards the staple anvil and moves to a maximum displacement position, where t is a dimension of a crossbeam portion of the staple in the direction perpendicular to the cartridge surface.

* * * * *